United States Patent [19]

Schuurs et al.

[11] 4,016,043

[45] Apr. 5, 1977

[54] ENZYMATIC IMMUNOLOGICAL METHOD FOR THE DETERMINATION OF ANTIGENS AND ANTIBODIES

[75] Inventors: Antonius H. W. M. Schuurs; Bauke K. Van Weemen; Gerrit Wolters, all of Oss, Netherlands

[73] Assignee: Akzona Incorporated, Asheville, N.C.

[22] Filed: Sept. 4, 1975

[21] Appl. No.: 610,469

[52] U.S. Cl. .................. 195/103.5 R; 195/127; 195/99

[51] Int. Cl.$^2$ .......................................... C12K 1/04

[58] Field of Search ............... 195/103 JR, 99; 23/230 B

[56] References Cited

UNITED STATES PATENTS

| 3,791,932 | 2/1974 | Schums et al. | 195/103.5 R |
|---|---|---|---|
| 3,852,157 | 12/1974 | Rubenstein et al. | 195/103.5 R |
| 3,876,504 | 4/1975 | Koffler | 195/103.5 R |
| 3,896,217 | 7/1975 | Johnson | 23/230 B |
| 3,905,767 | 9/1975 | Morris et al. | 195/103.5 R |

Primary Examiner—A. Louis Monacell
Assistant Examiner—C. A. Fan
Attorney, Agent, or Firm—Francis W. Young; Hugo E. Weisberger

[57] ABSTRACT

The present invention relates to improvements in the sandwich technique for the determination of a component of an antigen-antibody reaction in a liquid sample to be tested, utilizing as reagents (a) one component of said reaction bound to the surface of a water-insoluble, water-insuspensible, solid carrier, and (b) a component having the same immunological properties covalently linked to an enzyme. The liquid sample is contacted and incubated with the reagent(s) to form a reaction mixture, the enzyme activity of either the liquid or solid phase of which is a measure of the presence and quantity of the component to be determined. The method is especially useful for diagnostic testing for hepatitis or rubella antibodies.

8 Claims, 1 Drawing Figure

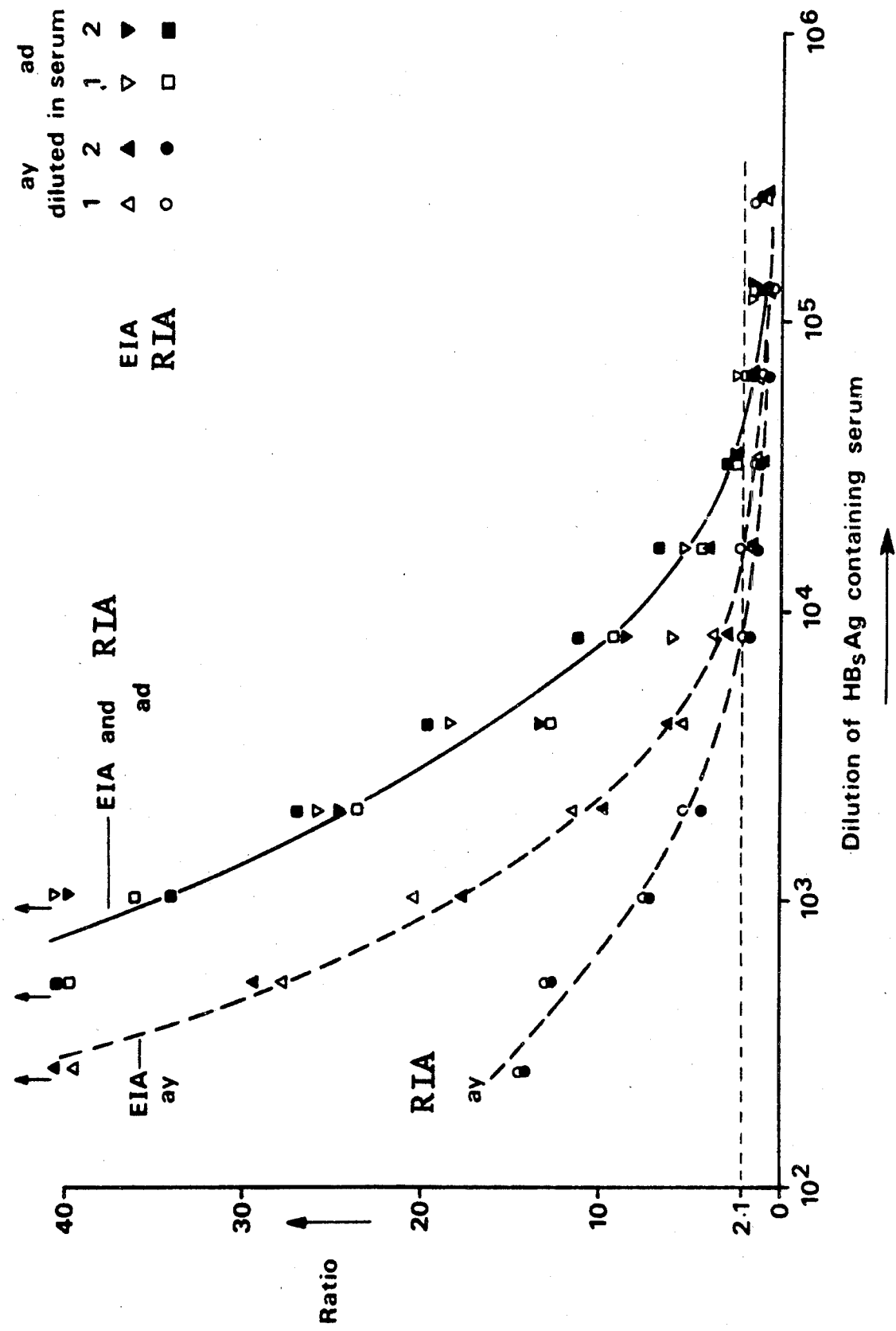

ENZYMATIC IMMUNOLOGICAL METHOD FOR THE DETERMINATION OF ANTIGENS AND ANTIBODIES

BACKGROUND OF THE INVENTION

This invention relates to a diagnostic method for the direction and determination of antigens and antibodies. More particularly, this invention relates to diagnostic methods for the detection and determination of pathogenic disease antigens and antibodies, such as hepatitis and rubella antigens and their associated antibodies.

A number of immunological methods have been developed for the determination of antigens and antibodies, including methods for the determination of hepatitis B surface antigen ($HB_sAg$), a component of hepatitis B virus and its associated antibodies.

In this field it is important that whatever methods are used are as sensitive and reliable as possible since an incorrect diagnosis can have serious consequences. This is especially true of the determination of hepatitis antigens and their associated antibodies since the transmission of the hepatitis virus via blood donors constitutes a significant public health risk.

Up to the present time, the radio-immunoassay (RIA) method in its various forms has been the most sensitive system available. This method has several disadvantages, however, including the requirement of special equipment, trained staff, the need for extra safety measures to protect against harmful radiation, and the short half-life span of the radioactive labelling element. The possibility of replacing the radioactive label with an enzyme label was proposed in 1968 in an article by L. E. M. Miles and C. N. Hales, entitled "Labelled Antibodies and Immunological Assay Systems," Lancet, London 1968 II, page 492; Nature, Vol. 219, pages 186-189 (July 13, 1968), but no procedural details were provided, the article failing to offer more than the general idea, leaving it to future workers to determine the basic steps and to perform the extensive experimentation needed to establish a practical operative enzymic immunoassay method.

The pioneering work on enzyme-immunoassay (EIA) methodology was performed by Schuurs and coworkers, and is disclosed in a series of their U.S. Pat. Nos. 3,654,090, 3,791,932, 3,850,752, 3,839,153, and 3,879,262.

In the course of the further evolution of the radio-immunoassay procedures by numerous workers, it was pointed out out in an article by E. Habermann, entitled "A new Principle for the Quantitative Determination of High Molecular Antigens (Junction Test), etc." published in Z. klin. Chem. u. klin. Biochem., 8th year, January, 1970, pages 51-55, that those methods based on the competition of radio-labelled and unlabelled antigens for a limited amount of antibodies gave better results than other methods.

The Habermann article proposed an RIA method in which in a first step, the antigen is adsorbed on an antibody fixed with a covalent bond by a solid phase, e.g., cellulose; a second step consists in fixing by labelled antibodies those antigen determinants remaining accessible. The non-fixed component of the antibody preparation is removed by washing. The radioactivity of the solid phase is correlated with the antigen content of the original solution. Since the labelled and solid phase antibodies are joined via the antigen, the author called the technique the "junction test." This arrangement is also known in the art as the "sandwich technique or method." The Habermann article, referred to the earlier suggestion of Miles and Hales (loc. cit.), and contained a passing suggestion that the test could be improved in sensitivity by coupling the antibody molecule with an easily detectable enzyme, but also offered no further suggestions, leaving it to others to develop such an enzyme method.

In Schuurs et al. U.S. Pat. No. 3,791,932, there is disclosed, in Example III, a rudimentary sandwich-type procedure for the determination of human chorionic gonadotropin (HCG) and luteinizing hormone (LH) in low concentrations by means of an enzyme-antibody coupling component, in accordance with which a predetermined amount of HCG is first coupled to a solid immuno-adsorbent (m-aminobenzyloxymethyl cellulose). Antibodies from rabbit anti-HCG serum are then coupled to an enzyme (horse radish peroxidase, HRP) and the coupling product is bound to HCG cellulose. HCG and LH dilution series are mixed with anti-HCG cellulose to form an immunoadsorbent, to which a given amount of the antibody-enzyme coupling product is added, and the enzyme activity of the supernatant liquid is determined. This procedure is somewhat involved and requires a number of coordinated operating steps.

It is an object of the present invention to develop and further improve and simplify the early version of the sandwich technique as applied to the determination of antigens and antibodies.

GENERAL DESCRIPTION OF THE INVENTION

In accordance with the present invention, there is provided a novel, very simple and sensitive enzyme immunoassay (EIA) test system especially adapted for the detection and determination of a component of an antigen-antibody reaction. The general principle of the procedure of the invention is that of employing as a test reagent a given amount of one component of said reaction bound to the surface of a water-insoluble, water-insuspensible solid carrier, and as a second reagent, a given amount of the same component covalently linked to an enzyme. The liquid sample containing the component to be determined is contacted with these reagents. In case the component to be determined and the component bound to the solid carrier are the same, a given amount of a binding partner of said component is added to the liquid sample. Upon mixing the reagents and the sample, there is formed a reaction mixture having a solid phase and a liquid phase. Finally the enzyme activity of the solid or liquid phase is determined, said activity being a measure of the presence and quantity of the component to be determined.

The enzyme-immunoassay (EIA) method according to the present invention does not possess the disadvantages of a radioimmunoassay method, and is simpler to set up and perform than the earlier EIA methods, but, surprisingly, is as sensitive as the RIA method. One of the advantages of the EIA according to the present invention is that by using an enzyme as a labelling means the immunological reaction can be measured by a color reaction. Either a colored substrate or a colored end-product should participate in the enzyme-catalyzed reaction so that the detection can take place by reading with the naked eye or by measurement of the extinction.

More specifically, the method of the present invention comprises contacting a liquid sample, for example serum or plasma, containing an unknown amount of antigen or antibody, with a predetermined amount of either the antigen or the antibody, which is bound to the surface of a water-insoluble, water-insuspensible, solid carrier. The liquid sample is then incubated with this coated solid carrier for a period of 0.5 to 35 hours, usually at a temperature between 4° and 50° C. After aspiration and washing, the foregoing solid phase is contacted with an amount of the same component covalently linked to an enzyme. If the component to be determined in the liquid sample, and the component coupled to the solid carrier are the same, the solid phase is contacted with a binding partner for the component to be determined.

The binding partner is employed in an insoluble form. The determination can take place by adding the binding partner in an insoluble form, or it can be added in a dissolved form, and insolubilized afterwards. The binding partner is preferably a protein capable of binding the antigen or antibody specifically.

After an incubation period, usually from 0.5 to 25 hours, and at a temperature between 4° and 50° C, aspiration and washing, the enzymatic activity bound to the solid phase is determined, which activity is a measure of the pressure of the antigen or antibody component in the liquid sample tested.

Both for the detection and quantitative determination of the antigen or antibody, the foregoing reagents are employed in predetermined amounts.

The solid carrier to which one of the components is bound may be any water-insoluble, water-insuspensible, solid carrier. Examples of suitable solid carriers include large beads, e.g., of polystyrene, filter paper, test tubes, and microtiter plates. The immunological component may be bound to the solid carrier by covalent bonds or by adsorption. The advantage of the use of a solid carrier is that no centrifugation step is needed for the separation of solid and liquid phase.

As a solid carrier, use is preferably made of a test tube of a microtiter plate the inner walls of which are coated with the immunological component.

The antigen or antibody enzyme conjugate consists of the immunological component covalently linked to one or more enzyme molecules. Such linking can be achieved either by direct condensation or by using external bridging molecules, in accordance with methods known to those skilled in the art.

Thus, the production of enzyme coupling products employing a covalent bond can be effected by reagents such as carbodiimides, diisocyanates, glutaric aldehyde, and bis-diazobenzidine.

The choice of the enzyme that is to form a part of the coupling product is determined by properties such as the specific binding activity (a high conversion rate increases the sensitivity of the test system) and the simplicity of determination of the enzyme. The determination of an enzyme catalyzing a conversion in which colored reaction components are invovled, is simple. Such colorimetric determinations can be automatic in a simple manner. It is also possible to employ enzymes catalyzing those conversions in which reaction components are involved that can be determined spectrophotometrically or fluorimetrically. These determinations are also suitable for automation, which is an additional advantage.

As enzymes suitable for the method of the invention there can be employed catalase, peroxidase, urease, glucose oxidase, alkaline phosphatase. Horse radish peroxidase is preferred.

The method according to the present invention can be used for the detection and determination of antigens and antibodies in general, including bacteria, viruses, hormones, proteins and their associated antibodies, but is particularly suited for the detection and determination of hepatitis B surface antigen and rubella and their associated antibodies. The invention will be illustrated with respect to these examples but is not to be considered as limited thereto.

In order to compare the enzyme-immunoassay of the invention with the corresponding radio-immunoassay, for the detection of $HB_sAg$, two $HB_sAg$-containing sera (1 subtype *ad*, 1 subtype *ay*) were taken and were diluted in two different normal sera, free from $HB_sAg$ and anti-$HB_s$. The results from these four dilution series are indicated in the accompanying drawing. They demonstrate that EIA and RIA have about the same sensitivity, but that the EIA gives a steeper dose-response curve with the serum containing subtype *ay*.

The enzyme immunoassay for $HB_sAg$ according to the present invention detected all antigen-positive samples "A," "B" and "C" of the NIH reference panel No. 2, both by eye reading and extinction measurement. This means that the assay system according to the present invention has at least "third generation" sensitivity as defined in the Federal Register, Vol. 39, No. 132, of July 9, 1974.

DESCRIPTION OF THE PREFERRED EMBODIMENTS

The following examples serve to illustrate the practice of the invention, but are not to be regarded as limiting:

EXAMPLE I

Detection of Hepatitis B Surface Antigen In Human Serum or Plasma 0.1 ml test sample (human serum or plasma) is added to each well of a polystyrene microtiter plate to the inner walls of which sheep anti-(Hepatitis B surface antigen) is bound. The plate is incubated for 2 hours at 37° C. The wells are emptied by aspiration. Each well is washed three times with 0.2 ml 0.2 M TRIS (trihydroxy-methylaminomethane; 2-amino-2-hydroxymethyl-1,3-propanediol) buffer, pH 7.4 (buffer A). 0.1 ml Horse radish peroxidase coupled to sheep anti-(Hepatitis B surface antigen) in a predetermined dilution in Buffer A is added. The plate is incubated for 2 hours at 37° C. The wells are emptied by aspiration. Each well is washed four times with 0.2 ml buffer A. 0.1 ml of a substrate solution of:

0.4 mg orthophenylene diamine per ml
0.2 mg urea-peroxidase per ml
in a McIlvain buffer of pH 5.0 is added to each well. The plate is incubated for 60 minutes at room temperature. The reaction is stopped by adding 0.05 ml of 0.5 N sulphuric acid. The color is read by eye or measured colorimetrically at 492 nm.

A result is called positive if the ratio is $\geq$ 2.1, i.e., the average extinction is at least 2.1 times the average extinction of six negative control sera.

Result A

Titration of two Hepatitis B surface antigen-positive sera of the *ay* and *ad* subtypes in enzyme immunoassay and a radio-immunoassay licensed by the U.S. Federal Drug Administration. The positive sera were diluted in two sera negative for Hepatitis B surface antigen and for anti-(Hepatitis B surface antigen), so that the serum concentration was the same in all dilutions. The curves of the ad subtype in both tests are represented by one line. (See accompanying drawing).

Result B

Reaction of the NIH Reference panel No. 2 in the abovementioned assay system.

| lot No. | ratio | eye-reading | lot No. | ratio | eye-reading |
|---------|-------|-------------|---------|-------|-------------|
| 201 | >26. | + | 227 | 1.36 | − |
| 202 | >26. | + | 228 | >26. | + |
| 203 | 0.97 | − | 229 | 1.51 | − |
| 204 | 10.33 | + | 230 | 1.72 | − |
| 205 | >26. | + | 231 | 1.51 | − |
| 206 | >26. | + | 232 | >26. | + |
| 207 | 1.79 | − | 233 | 1.15 | − |
| 208 | >26. | + | 234 | >26. | + |
| 209 | >26. | + | 235 | >26. | + |
| 210 | >26. | + | 236 | 1.56 | − |
| 211 | 1.11 | − | 237 | 1.16 | − |
| 212 | 1.25 | − | 238 | >26. | + |
| 213 | >26. | + | 239 | >26. | + |
| 214 | >26. | + | 240 | 1.39 | − |
| 215 | 2.05 | − | 241 | 1.38 | − |
| 216 | 1.32 | − | 242 | 1.23 | − |
| 217 | >26. | + | 243 | >26. | + |
| 218 | >26. | + | 244 | >26. | + |
| 219 | >26. | + | 250 | >26. | + |
| 220 | >26. | + | 251 | >26. | + |
| 224 | 1.04 | − | 252 | >26. | + |
| 225 | 1.16 | − | 253 | >26. | + |
| 226 | >26. | + | 254 | >26. | + |
| 255 | >26. | + | | | |
| 256 | >26. | + | | | |
| 260 | >26. | + | | | |
| 261 | >26. | + | | | |

EXAMPLE II

Detection of antibodies against hepatitis B surface antigen in human serum of plasma 0.1 ml test sample (human serum or plasma) is added to each well of a polystyrene microtiter plate to the inner walls of which sheep anti-(Hepatitis B surface antigen) is bound. 0.05 ml of a predetermined dilution of hepatitis B surface antigen in 0.2 M TRIS buffer pH 7.4 is added to each well. The plate is incubated for 2 hours at 37° C and treated further in the same way as in Example I.

Results

Extinction after testing a dilution series of an anti-(hepatitis B surface antigen)-containing serum in antigen-and antibody-negative serum and six antigen- and antibody-negative control sera.
Serum positive for anti-(Hepatitis B surface antigen)

A reaction is called positive is the extinction is ≤ 50% of the average extinction of 6 negative control sera.

EXAMPLE III

Detection of antibodies against Rubella virus in human serum or plasma 0.5 ml of test sample (human serum or plasma) is added to polystyrene tubes $\phi$ 1 cm to the inner walls of which inactivated Rubella virus is coupled. The tubes are incubated for 1 hour at 37° C. The tubes are emptied by aspiration. Each tube is washed three times with 2 ml 0.15 M phosphate buffer. 0.5 ml horse radish peroxidase coupled to inactivated Rubella virus in a predetermined dilution in 0.2 M TRIS buffer + 0.1% triton $X_{100}$ is added. The tubes are incubated for 3 hours at 37° C. Each tube is washed three times with 2 ml 0.2 M TRIS buffer + 0.1% triton $X_{100}$. The horse radish peroxidase activity is determined by adding 0.5 ml substrate solution (see example I) and incubating for 60 minutes at 37° C. The reaction is stopped by adding 0.25 ml of 0.5 N sulphuric acid. The color is measured colorimetrically at 494 nm. A result is called positive if the ratio is ≥ 2.9, i.e., the average extinction is at least 2.9 times the average extinction of 8 negative control sera.

Results

Extinction after testing a dilution series of an anti-(Rubella-virus)-containing serum in serum negative for Rubella virus and anti-(rubella virus), and eight negative control sera.
Serum positive for anti-rubella-virus:

| Undiluted | 1/2 | 1/4 | 1/8 | 1/16 | 1/32 | 1/64 | 1/128 |
|-----------|-----|-----|-----|------|------|------|-------|
| 0.050 | 0.051 | 0.049 | 0.062 | 0.060 | 0.058 | 0.168 | 0.200 |
| 1/256 | 1/512 | | | | | | |
| 0.203 | 0.198 | | | | | | |
| Negative control sera undiluted: | | | | | | | |
| serum No. | 1 | 2 | 3 | 4 | 5 | 6 | |
| | 0.201 | 0.197 | 0.232 | 0.205 | 0.212 | 0.218 | |

| 1/32 | 1/64 | 1/128 | 1/256 | 1/512 | 1/1024 | 1/2048 | 1/4096 |
|---|---|---|---|---|---|---|---|
| >2.000 | >2.000 | >2.000 | 1.653 | 0.985 | 0.499 | 0.285 | 0.175 |
| 1/8192 | 1/16384 | | | | | | |
| 0.103 | 0.095 | | | | | | |

Negative control sera undiluted:

| serum No. | 1 | 2 | 3 | 4 | 5 | 6 | 7 | 8 |
|---|---|---|---|---|---|---|---|---|
| | 0.058 | 0.092 | 0.070 | 0.101 | 0.085 | 0.063 | 0.058 | 0.082 |

EXAMPLE IV

Detection of rubella virus in human serum or plasma 0.5 ml of test sample (human serum or plasma) is added to 0.1 ml of a predetermined solution of rabbit anti-rubella-virus. The mixture is incubated for 1 hour at 37° C. 0.5 ml of this mixture is added to a polystyrene tube $\phi$ 1 cm to the inner walls of which inactivated rubella virus is bound. The tubes are incubated for 1 hour at 37° C and treated further in the same way as in Example III.

Results

Extinctions after testing a dilution series of a rubella virus-containing serum in serum negative for rubella-virus and anti-rubella-virus.

Serum positive for rubella virus:

| 1/100 | 1/200 | 1/400 | 1/800 | 1/1600 | 1/3200 | 1/6400 | 1/12800 |
|---|---|---|---|---|---|---|---|
| 0.075 | 0.076 | 0.073 | 0.090 | 0.088 | 0.097 | 0.201 | 0.252 |
| 1/25600 | | | | | | | |
| 0.0249 | | | | | | | |

Negative control sera undiluted:

| serum No. | 1 | 2 | 3 | 4 | 5 | 6 | 7 | 8 |
|---|---|---|---|---|---|---|---|---|
| | 0.250 | 0.238 | 0.278 | 0.275 | 0.263 | 0.291 | 0.0258 | 0.261 |

A reaction is called positive if the extinction is ≤ 50% of the average extinction of 8 negative control sera.

For the performance of the method according to the invention, a test pack or kit of the reagents is preferably employed, chiefly composed of:

a. a given quantity of a component of the antigen-antibody reaction bound to a water-insoluble, water-insuspensible solid carrier;

b. a substance having the same immunological properties as said component, covalently linked to an enzyme;

c. the binding partner of the component to be determined if the component has the same immunological properties as the component in (a). According to their nature, these reagents can be preserved by freeze-drying or dissolved in a buffer. Thus, a specific test pack may comprise (a) the antibody against hepatitis B surface antigen coupled to a water-insoluble, water-insuspensible, solid carrier; (b) said antibody covalently linked to an enzyme; and (c) hepatitis B surface antigen in case the component to be determined is the antibody against hepatitis antigen.

What is claimed is:

1. A method for the detection and determination of a component of an antigen-antibody reaction in a liquid sample containing the component to be determined, comprising the steps of:

a. providing a given quantity of a first reagent consisting of one component of said reaction selected from the group consisting of an antigen and an antibody bound to the surface of a water-insoluble, water-insuspensible, solid carrier;

b. providing a given amount of a second reagent consisting of a component having the same immunological properties as the component in the said first reagent covalently linked to an enzyme, and also providing a predetermined amount of the binding partner for the component to be determined, when the component in said liquid sample and the component bound to said solid carrier have the same immuno-chemical properties;

c. contacting a given quantity of said liquid sample with said reagents forming a reaction mixture having a solid phase and a liquid phase; and d. determining the enzyme activity of either the solid or the liquid phase which is a measure of the presence and quantity of the component to be determined.

2. A method for determining the presence of a component of an antigen-antibody reaction in a liquid sample containing the component to be determined comprising the steps of:

a. providing a given quantity of a first reagent consisting of one component of said reaction selected from the group consisting of an antigen and an antibody bound to the surface of water-insoluble, water-insuspensible, solid carrier, and also providing a predetermined amount of the binding partner for the component to be determined when the component in said liquid sample and the component bound to said solid carrier have the same immunochemical properties;

b. contacting and incubating a given quantity of said liquid sample with said first reagent;

c. washing said solid carrier;

d. providing a given quantity of a substance having the same immunological properties as the component previously bound to the solid carrier, said substance being covalently linked to an enzyme;

e. contacting and incubating the solid phase from step (c) with said enzyme-linked substance;

f. washing the solid carrer; and g. determining the enzyme activity substance bound to the solid phase, which is a measure of the presence and quantity of the component to be determined.

3. The method of claim 2 wherein said liquid sample and the binding partner of the component to be determined are preincubated with each other, before contacting the sample with said solid carrier.

4. A method for the detection and determination of a component in the reaction of a hepatitis antigen and the associated antibody in a liquid sample containing said component, comprising the steps of:
   a. providing a given quantity of a reagent consisting of one component of said reaction selected from the group consisting of said antigen and said antibody bound to a water-insoluble, water-insuspensible, solid carrier;
   b. contacting and incubating said liquid sample with said solid carrier of step (a) to form a reaction mixture;
   c. providing a given quantity of a substance having the same immunological properties as the component bound to said solid carrier, said substance being covalently linked to an enzyme, and also providing a predetermined amount of the binding partner for the component to be determined when the component in said liquid sample and the component bound to said solid carrier have the same immunochemical properties;
   d. contacting and incubating the reaction mixture with said enzyme-linked substance; and
   e. determining the enzyme activity of substance bound to the solid phase, which is a measure of the presence and quantity of the component to be determined.

5. The method of claim 4 in which said hepatitis antigen is hepatitis B surface antigen, and the antibody is its associated antibody.

6. The method of claim 4 in which said solid carrier is washed after the incubation of the liquid sample with the immunological component bound to the solid carrier.

7. A diagnostic pack for the detection and determination of a component of an antigen-antibody reaction selected from the group consisting of an antigen and an antibody, consisting of:
   a. one of said components coupled to a water-insoluble, water-insuspensible, solid carrier;
   b. a substance having the same immunological properties as the component in (a) covalently linked to an enzyme; and
   c. the binding partner of the component to be determined if the component to be determined has the same immunological properties as the component in (a).

8. A diagnostic pack for the detection and determination of hepatitis B consisting of:
   a. the antibody against Hepatitis B surface antigen coupled to a water-insoluble, water-insuspensible, solid carrier;
   b. said antibody covalently linked to an enzyme; and
   c. Hepatitis B surface antigen in case the component to be determined is the antibody against Hepatitis antigen.

* * * * *

Disclaimer 4,016,043.—*Antonius H. W. M. Schuurs, Bauke K. Van Weemen,* and *Gerrit Wolters,* Oss, Netherlands. ENZYMATIC IMMUNOLOGICAL METHOD FOR THE DETERMINATION OF ANTIGENS AND ANTIBODIES. Patent dated Apr. 5, 1977. Disclaimer filed June 20, 1977, by the assignee, *Akzona Incorporated.*

The term of this patent subsequent to February 12, 1991, has been disclaimed.

[*Official Gazette October 18, 1977.*]

Notice of Adverse Decision in Interference

In Interference No. 99,978, involving Patent No. 4,016,043, A. H. W. M. Schuurs, B. K. Van Weemen and G. Wolters, ENZYMATIC IMMUNOLOGICAL METHOD FOR THE DETERMINATION OF ANTIGENS AND ANTIBODIES, final judgment adverse to the patentees was rendered May 23, 1983, as to claim 2.

[*Official Gazette November 8, 1983.*]